United States Patent
Akashi et al.

(10) Patent No.: US 8,029,920 B2
(45) Date of Patent: *Oct. 4, 2011

(54) 1,3,5-TRIS(DIARYLAMINO)BENZENES AND USE THEREOF

(75) Inventors: Nobutaka Akashi, Kobe (JP); Hideyuki Katou, Kobe (JP)

(73) Assignee: Bando Chemical Industries, Ltd, Hyogo (JP)

( * ) Notice: Subject to any disclaimer, the term of this patent is extended or adjusted under 35 U.S.C. 154(b) by 256 days.

This patent is subject to a terminal disclaimer.

(21) Appl. No.: 12/282,266

(22) PCT Filed: Mar. 8, 2007

(86) PCT No.: PCT/JP2007/055166
§ 371 (c)(1),
(2), (4) Date: Sep. 9, 2008

(87) PCT Pub. No.: WO2007/105783
PCT Pub. Date: Sep. 20, 2007

(65) Prior Publication Data
US 2009/0058287 A1  Mar. 5, 2009

(30) Foreign Application Priority Data
Mar. 13, 2006 (JP) ................. 2006-067768

(51) Int. Cl.
C07C 211/43 (2006.01)
H01J 1/63 (2006.01)
H01L 51/54 (2006.01)
(52) U.S. Cl. ........ 428/690; 428/917; 313/504; 313/506; 564/307
(58) Field of Classification Search ........... None
See application file for complete search history.

(56) References Cited

U.S. PATENT DOCUMENTS
| | | | |
|---|---|---|---|
| 7,629,059 B2 * | 12/2009 | Akashi et al. | 428/690 |
| 2005/0184657 A1 * | 8/2005 | Kato et al. | 313/504 |
| 2007/0224449 A1 * | 9/2007 | Kato et al. | 428/690 |
| 2008/0048952 A1 * | 2/2008 | Hanaki et al. | 345/82 |
| 2010/0006828 A1 * | 1/2010 | Kobata et al. | 257/40 |

FOREIGN PATENT DOCUMENTS
| | | |
|---|---|---|
| JP | 8-291115 A | 7/1999 |
| JP | 11-174707 A | 7/1999 |
| JP | 11-329734 A | 11/1999 |
| JP | 2004-277385 A | 10/2004 |
| JP | 2005-190993 A | 7/2005 |
| JP | 2005-276802 A | 10/2005 |
| JP | 2007-088430 A | 4/2007 |

OTHER PUBLICATIONS
International Search Report for PCT/JP2007-055166, dated Jun. 5, 2007.

* cited by examiner

*Primary Examiner* — Dawin L. Garrett
(74) *Attorney, Agent, or Firm* — Hamre, Schumann, Mueller & Larson, P.C.

(57) ABSTRACT

The invention provides a 1,3,5-tris(diarylamino)benzene represented by the general formula (I)

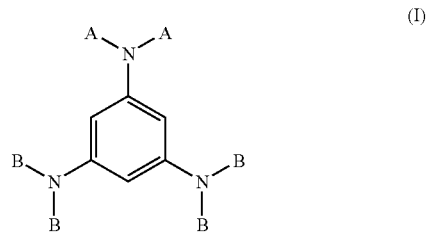

wherein A and B are each independently a group represented by the general formula (II)

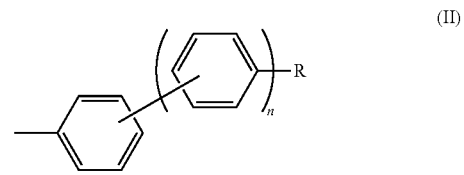

in which R is a hydrogen atom, an alkyl group of 1-6 carbons or a cycloalkyl group of 5 or 6 carbons and n is 0, 1, 2 or 3, provided that the values of n of A and B are not the same to each other. Such a 1,3,5-tris(diarylamino)benzene is able to form an amorphous film by vacuum evaporation at a relatively low temperature with almost or substantially no thermal decomposition, and is preferably used as organo-electronic functional material, in particular, as a hole injecting agent or a hole transporting agent.

8 Claims, 9 Drawing Sheets

1,3,5-TRIS(DIARYLAMINO)BENZENES AND USE THEREOF

FIELD OF THE INVENTION

The invention relates to a novel 1,3,5-tris(diarylamino)benzene and use thereof. More particularly, the invention relates to a novel 1,3,5-tris(diarylamino)benzene in which all the substituents on the nitrogen atoms of the three diarylamino groups are not the same, and accordingly which is able to form thin film by vacuum evaporation at a relatively low temperature with almost or substantially no thermal decomposition. The invention further relates to use of the 1,3,5-tris(diarylamino)benzene, in particular, as an organo-electronic functional material.

BACKGROUND ART

In recent years, a variety of electronic devices such as light-emitting elements or organic semiconductors in which an organic compound which has photoelectric function as well as reversible oxidation-reduction characteristics and can form amorphous film by itself is used as an organo-electronic material, for example, as a hole transporting agent, have attracted considerable attention. Such an amorphous film of organic compound is formed by preparing a coating composition comprised of a binder resin such as polycarbonate resin and the organic compound dissolved in a suitable organic solvent and then by coating and drying the composition (JP-A-11-174707). In the case of a polynuclear aromatic tertiary amine called a "star-burst" compound, it is vacuum evaporated onto a substrate to directly form a thin film (JP-A-08-291115).

According to a method using a binder resin among the methods mentioned above, the organic compound is diluted with the binder resin in the resulting thin film and influenced by the binder resin so that the organic compound cannot exhibit sufficiently the functions that it originally has as an organo-electronic functional material. In addition, if the organic compound forms a thin film that is stable at normal temperature with the aid of a binder resin, the organic compound has a low glass transition temperature so that the film is poor in heat resistance and has a problem in stability and life.

Under these circumstances, polynuclear aromatic tertiary amine compounds called the "star-burst" molecules are attracting considerable attention as organo-electronic functional materials since they are capable of forming stable thin film by vacuum evaporation. The star-burst molecules are divided into three groups based on their molecular structures: compounds having a triphenylamine structure (triphenylamines), compounds having a triaminobenzene structure (triaminobenzenes) and compounds having a triphenylbenzene structure (triphenylbenzenes).

A variety of "star-burst" molecules inclusive of the triaminobenzenes have been proposed. For example, as such triaminobenzenes, 1,3,5-tris(N-(p-methylphenyl)-N-(1-naphthyl))-amino benzene (p-MTPNAB) and 1,3,5-tris(N-(p-methylphenyl)-N-(4-biphenylyl)amino)benzene (p-MTPBAB) have been proposed (JP-A-2004-155754) These triaminobenzenes are reversible in oxidation-reduction process and have high relatively high glass transition temperatures, i.e., 87° C. and 98° C., respectively. However, there is still a fear that they have not enough stability in performance and durability for use as organo-electronic functional material.

Recently there have been proposed 1,3,5-tris(N-(4'-methyl-4-biphenylyl)-N-(4-methylphenyl)amino)benzene (JP-A-2005-190993) represented by the formula (1)

and 1,3,5-tris(N,N-bis(4'-methyl-4-biphenylyl)amino)benzene (JP-A-2005-276802) represented by the formula (2)

These 1,3,5-tris(diarylamino)benzenes are excellent in stability of repeated oxidation-reduction process compared with the triaminobenzenes which have hitherto been known, and have a higher glass transition temperatures. On the other hand, in these 1,3,5-tris-(diarylamino)benzenes, all the three diarylamino groups have the same chemical structure, that is, all the substituents which the three diaryl amino groups have are the same. Thus, these 1,3,5-tris-(diarylamino)benzenes have symmetry in molecular structure and high crystallinity, and accordingly, they have high melting points. As results, they need high evaporation temperature when they are vacuum evaporated to form thin film. Therefore, there is a problem that these 1,3,5-tris(diarylamino)benzenes thermally decompose when they are vacuum evaporated to form thin film.

The invention has been accomplished to solve the above-mentioned problems involved in the 1,3,5-tris(diarylamino)-benzenes which have heretofore been known. Accordingly, it is an object of the invention to provide a novel 1,3,5-tris(diarylamino)benzene which has characteristics excellent as organic electronic functional material, and which in addition can form thin film by vacuum evaporation at a relatively low temperature. It is a further object of the invention to provide an organic electronic functional material, in particular, a hole injecting and/or transporting agent which comprises such a 1,3,5-tris(diarylamino)benzene.

SUMMARY OF THE INVENTION

The invention provides a 1,3,5-tris(diarylamino)benzene represented by the general formula (I)

wherein A and B are each independently a group represented by the general formula (II)

in which R is a hydrogen atom, an alkyl group of 1-6 carbons or a cycloalkyl group of 5 or 6 carbons and n is 0, 1, 2 or 3, provided that the values of n of A and B are not the same to each other.

In particular, the invention provides a tris(diarylamino)benzene represented by the general formula (III)

wherein $R_1$ and $R_2$ are each independently a hydrogen atom, an alkyl group of 1-6 carbons or a cycloalkyl group of 5 or 6 carbons, as one of preferred 1,3,5-tris(diarylamino)benzenes of the invention.

The invention also provides a 1,3,5-tris(diarylamino)benzene represented by the general formula (IV)

wherein $R_1$ and $R_2$ are each independently a hydrogen atom, an alkyl group of 1-6 carbons or a cycloalkyl group of 5 or 6 carbons, as a further one of preferred 1,3,5-tris(diarylamino)benzenes of the invention.

The invention further provides an organic electronic functional material comprising the above-mentioned 1,3,5-tris(diarylamino)benzene. Such an organic electronic functional material can be preferably used, for example, as a hole injecting and/or transporting agent. Accordingly, the invention provides an organic electroluminescence element which comprises a hole injecting and/or transporting layer comprising a hole injecting and/or transporting agent comprising the above-mentioned 1,3,5-tris(diarylamino) benzene as a preferred embodiment of the invention.

THE BEST MODES FOR CARRYING OUT THE INVENTION

The 1,3,5-tris(diarylamino)benzene according to the invention is represented by the general formula (I)

(I)

wherein A and B are each independently a group represented by the general formula (II)

(II)

in which R is a hydrogen atom, an alkyl group of 1-6 carbons or a cycloalkyl group of 5 or 6 carbons and n is 0, 1, 2 or 3, provided that the values of n of A and B are not the same to each other.

In the 1,3,5-tris(diarylamino)benzene represented by the general formula (I), the aryl groups A and B represented by the general formula (II) are each a phenyl group which may have the alkyl group or cycloalkyl group, a biphenylyl group which may have the alkyl group or cycloalkyl group at the terminal phenyl group, a terphenyl group which may have the alkyl group or cycloalkyl group at the terminal phenyl group, or a quaterphenyl group which may have the alkyl group or cycloalkyl group at the terminal phenyl group.

However, the aryl groups A and B represented by the general formula (II) do not have the same value of n at the same time according to the invention. Therefore, for example, when the aryl group A is a phenyl group (namely, n=0) which may have the above-mentioned substituent thereon, the aryl group B is a biphenylyl group (n=1), a terphenylyl group (n=2), or a quaterphenyl group (n=3) which may have the above-mentioned substituent. The aryl groups A and B may be a group opposite to each other in respect of the value of n.

On the other hand, when the aryl group A is, for example, a biphenylyl group (namely, n=1) which may have the above-mentioned substituent, the aryl group B is a phenyl group (n=0), a terphenylyl group (n=2), or a quaterphenyl group (n=3) which may have the above-mentioned substituent. The aryl groups A and B may be a group opposite to each other in relation to the value of n.

According to the invention, it is particularly preferred that one of the aryl groups A and B is a phenyl group which may have the above-mentioned substituent, and the other is a biphenylyl group which may have the above-mentioned substituent.

In the 1,3,5-tris(diarylamino)benzene represented by the general formula (I), when the group R is an alkyl group, it is, for example, a methyl, an ethyl, a propyl, a butyl, a pentyl, or a hexyl group, and when it is an alkyl group of three or more carbon atoms, it may be linear or branched. A cycloalkyl group is a cyclopentyl or a cyclohexyl group. It is particularly preferred that the group R is a hydrogen atom or a methyl group.

Further according to the invention, the 1,3,5-tris(diarylamino)-benzene represented by the general formula (I), when the group R is an alkyl or a cycloalkyl group on a phenyl group, it is preferred that the group is a substituent on the 4-position of the phenyl group, and when the group R is an alkyl or a cycloalkyl group on a biphenylyl group, it is preferred that the group is a substituent on the 4'-position of the biphenylyl group.

Accordingly, particularly preferred 1,3,5-tris(diarylamino)-benzenes of the invention among others are such that they are represented by the general formula (III)

(III)

wherein $R_1$ and $R_2$ are each independently a hydrogen atom or a methyl group, or by the general formula (IV)

(IV)

wherein $R_1$ and $R_2$ are each independently a hydrogen atom or a methyl group.

Examples of such preferred 1,3,5-tris(diarylamino)benzenes of the invention include, for example, N,N,N',N'-tetrakis(4'-methyl-4-biphenylyl)-N'',N'''-bis(4-methylphenyl)benzene-1,3,5-triamine represented by the formula (3)

(3)

N,N,N',N'-tetrakis(4-biphenylyl)-N'',N''-bis(4-methylphenyl)benzene-1,3,5-triamine represented by the formula (4)

(4)

and
N,N,N',N'-tetrakis(4-methylphenyl)-N'',N''-bis(4'-methyl-4-biphenylyl)-benzene-1,3,5-triamine represented by the formula (5)

(5)

The 1,3,5-tris(diarylamino)benzene of the invention can be prepared by a dehydrohalogenation reaction of one mole part of 1-(N,N-diaryl)amino-3,5-dihalobenzene and 2 mol parts of a diarylamine depending on the structure of the 1,3,5-tris(diarylamino)benzene.

In more detail, for example, N,N,N',N'-tetrakis(4'-methyl-4-biphenylyl)-N'',N''-bis(4-methylphenyl)benzene-1,3,5-triamine (3), can be obtained by reacting bis(N,N-4-methylphenyl)-3,5-dichlorophenylamine (6) with bis(4'-methylbiphenylyl)amine (7) using a palladium catalyst in the presence of a base in an organic solvent under an inert gas atmosphere, as shown in the scheme below. The base used in the reaction includes, for example, an alkali metal alkoxide such as sodium t-butoxide, and a carbonate or a hydrogen carbonate of an alkali metal such as potassium carbonate and potassium hydrogen carbonate. The reaction solvent used is preferably a hydrocarbon solvent such as xylene, decalin, mesitylene or heptane. The reaction temperature is usually in the range of 100-130° C., and the reaction time is usually in the range of 5-30 hours. After the completion of reaction, the reaction product is dissolved in an organic solvent and the catalyst used is separated by filtration, and then the reaction product is separated and purified by column chromatography using an appropriate eluate. The product may be further purified by recrystallization from a suitable organic solvent, thereby to provide a high purity product.

One of the three diarylamino groups of the 1,3,5-tris(diarylamino)benzene of the invention is different in chemical structure from the other two diarylamino groups. Thus, the compound has a high glass transition temperature and a high decomposition temperature. However, the compound is not completely symmetric in the molecular structure and has a relatively low melting point. As a result, the compound is able to form thin film by vacuum evaporation at a relatively low temperature with almost or substantially no thermal decomposition. In addition, since the thin film shows no clear peaks in X-ray diffraction analysis, the film is an amorphous film with no anisotropy. Accordingly, the 1,3,5-tris(diarylamino)benzene of the invention can form a stable amorphous film by itself at ordinary temperature or higher than that, namely, without the aid of a binder resin. Moreover, the 1,3,5-tris(diarylamino)benzene of the invention is excellent in solubility to an organic solvent.

Therefore, the 1,3,5-tris(diarylamino)benzene of the invention can be suitably used as an organo-electronic functional material in various electronic devices where heat resistance is required. Among various electronic devices, in particular, an organic electroluminescence element is driven by a direct current at a low electric voltage with high efficiency to emit light at a high luminance, as well as it can be made thin. Accordingly, in recent years, the investigation to put the organic electroluminescence element to practical use as display devices as well as backlights or illumination devices is pushed forward. The 1,3,5-tris(diarylamino)benzene of the invention can be suitably used as various organo-electronic functional materials for an organic electroluminescence element.

By way of examples, a hole injecting layer wherein the 1,3,5-tris(diarylamino)benzene of the invention is used as a hole injecting agent is formed between an anode and a hole transporting layer, or a hole transporting layer wherein the 1,3,5-tris(diarylamino)benzene is used as a hole transporting agent is formed between a hole injecting layer and an emitting layer, or a hole injecting/transporting layer wherein the 1,3,5-tris(diarylamino)benzene is used as a hole injecting/transporting agent is formed between a cathode and an emitting layer, thereby an organic electroluminescence element which is excellent in durability and can be driven at a low electric voltage can be obtained. However, needless to say, the 1,3,5-tris(diarylamino)benzene of the invention may be used to form a thin film as a hole injecting and/or transporting layer using a binder resin.

Thus, the 1,3,5-tris(diarylamino)benzene of the invention can be used as a hole injecting agent to form a hole injecting layer in an organic electroluminescence element. Accordingly, it can also be used as a hole transporting agent to form a hole transporting layer in an organic electroluminescence element, as a hole transporting layer has the same function as a hole injecting layer. Further, it can also be used as a hole injecting/transporting agent when a hole injecting layer and a hole transporting layer are formed as a single layer.

Namely, the 1,3,5-tris(diarylamino)benzene of the invention can be used as a hole injecting and/or transporting agent, and such a hole injecting and/or transporting agent can be used in order to form a hole injecting and/or transporting layer in an organic electroluminescence element.

Figure 1:
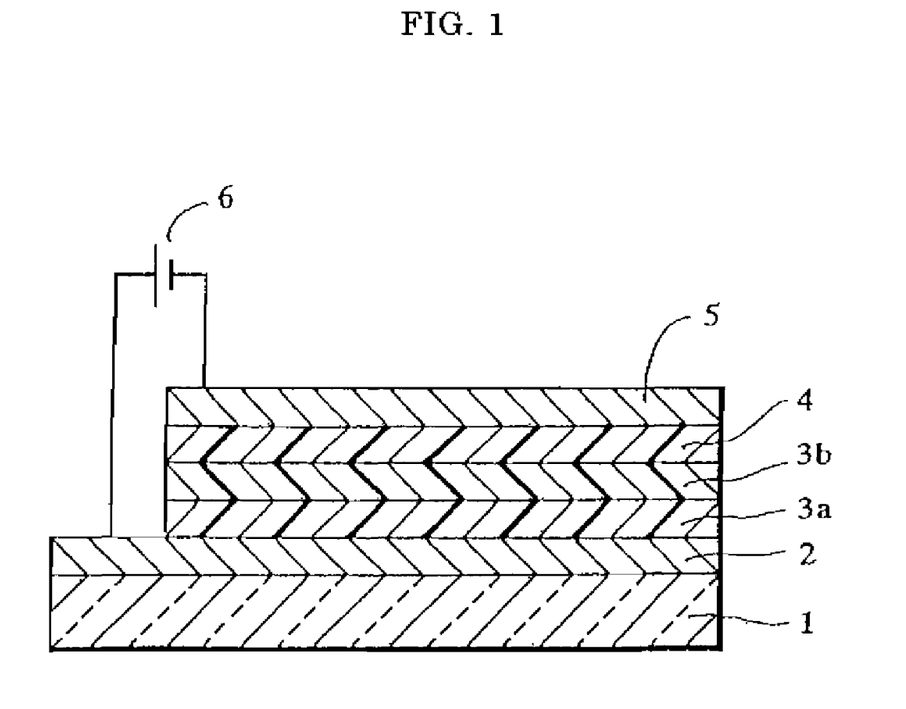
FIG. 1 is a cross section showing an example of an organic electroluminescence element.

As a preferred example of an electroluminescence element according to the invention is shown in FIG. 1, it comprises a transparent substrate 1 made of glass, for example, having an anode 2 made of a transparent electrode such as an ITO membrane (indium oxide-tin oxide membrane) laminated thereon, and a hole injecting layer 3a, a hole transporting layer 3, an emitting layer 4 and a cathode 5 made of a metal or a compound thereof laminated on the anode in this order. The anode and the cathode are connected with an external power source 6. In such an organic electroluminescence element as mentioned above, holes are readily injected from the anode into the emitting layer through the hole injecting layer and the hole transporting layer so that the organic electroluminescence element can be driven at a low electric voltage. Electrons are injected into the emitting layer from the cathode. The electrons injected from the cathode and the holes injected from the anode recombine in the emitting layer, and light is emitted and radiated outside through the transparent electrode (anode) and the transparent substrate.

In some cases, an electron transporting layer may be laminated between the emitting layer and the cathode, and a blocking layer may be formed in order to prevent excessive holes from passing through the emitting layer towards the cathode. The organic electroluminescence element is not specifically limited in layer structure.

The electroluminescence element of the invention is featured in that it has a hole injecting and/or transporting layer comprising the 1,3,5-tris(diarylamino)benzene of the invention. As mentioned hereinbefore, since the 1,3,5-tris(diarylamino)benzene of the invention can form an amorphous film by it self, a hole injecting layer can be formed by vacuum evaporation onto the transparent electrode using a vacuum evaporation device. The thickness of hole injecting layer is usually in the range of 10 nm to 200 nm, preferably in the range of 20 nm to 80 nm.

The 1,3,5-tris(diarylamino)benzene of the invention can be vacuum evaporated onto a hole injecting layer to form a hole transporting layer. The thickness of hole transporting layer is usually also in the range of 10 nm to 200 nm, preferably in the range of 20 nm to 80 nm. Further, a hole injecting and/or transporting layer in the form of single layer may be formed on the transparent electrode.

However, according to the invention, the 1,3,5-tris(diarylamino)-benzene of the invention may be dissolved in an appropriate organic solvent, if necessary, together with a binder resin, to prepare a solution, and then the solution may be coated on an anode by a spin coat method and dried to form a hole injecting and/or transporting layer. In this case also, the thickness of hole injecting and/or transporting layer is the same as that mentioned above.

In this way, a hole injecting layer is formed with the 1,3,5-tris-(diarylamino)benzene of the invention, and a hole transporting layer is formed with α-NPD etc. by a conventional method on the hole injecting layer, and then an emitting layer and a cathode are laminated on the hole transporting layer, thereby providing an organic electroluminescence element. In the same manner, a hole transporting layer is formed with the 1,3,5-tris(diarylamino)benzene of the invention on a hole injecting layer, and then an emitting layer and a cathode are formed on the hole injecting layer, thereby providing an organic electroluminescence element.

In the organic electroluminescence element of the invention, a transparent substrate, a common hole injecting and/or transporting layer which may be used in combination with the hole injecting and/or transporting layer of the invention, an anode, an emitting layer, an electron transporting layer and electrodes except the hole injecting and/or transporting layer formed of the 1,3,5-tris(diarylamino)benzene of the invention may be made of any conventionally known materials. For example, an anode may be made of indium oxide-tin oxide (ITO), and a cathode may be made of a metal such as aluminum, magnesium, indium or silver, or an alloy of these metals, such as Al-Mg alloy, Ag-Mg alloy, or lithium fluoride. A transparent substrate is usually made of glass.

For example, such a conventionally known low molecular weight organic compound as α-NPD (4,4'-bis(N-(1-naphthyl)-N-phenylamino)-biphenyl) and TPD (4,4'-bis(3-methylphenyl)-N-phenylamino)biphenyl) are used as a common hole transporting agent, while copper phthalocyanine etc. are used as a common hole injecting agent. The thickness is usually in the range of 10 nm to 200 nm. The emitting layer is usually formed of tris(8-quinolinol) aluminum ($Alq_3$) and has a thickness in the range of 10 nm to 200 nm. When the organic electroluminescence element contains an electron transporting layer, the layer has also a thickness in the range of 10 nm to 200 nm. When an electroconductive polymer layer is employed, it has also a thickness in the range of 10 nm to 200 nm.

The 1,3,5-tris(diarylamino)benzene of the invention is not specifically limited in use, and it can be suitably used as a hole injecting agent, a hole transporting agent, and a host agent in an emitting layer for an organic electroluminescence element, and in addition, as an organic semiconductor for a solar cell and a charge transporting material for an electrophotographic device.

INDUSTRIAL APPLICABILITY

One of the three diarylamino groups of the 1,3,5-tris-(diarylamino)benzene of the invention is different in chemical structure from the other two diarylamino groups, that is, the substituents on one of the three diarylamino groups are different from those of the other two diarylamino groups. Thus, although the 1,3,5-tris(diarylamino)benzene of the invention has a high glass transition temperature and a high decomposition temperature, it has a relatively low melting point since it is asymmetric in molecular structure. As a result, the 1,3, 5-tris-(diarylamino)benzene of the invention is able to form thin film by vacuum evaporation at a relatively low temperature with almost or substantially no thermal decomposition. Accordingly, the 1,3,5-tris(diarylamino)-benzene of the invention provides an organo-electronic functional material in the form of thin film which is excellent in heat resistance and stable in performance.

EXAMPLES

The invention is described in more detail with reference to examples, however, the invention is not limited thereto.

Example 1

(Synthesis of N,N,N',N'-tetrakis(4'-methyl-4-biphenylyl)-N'',N''-bis(4-methylphenyl)benzene-1,3,5-triamine(3))

600 mL of xylene was placed in a 1 L-capacity separable flask, and then 0.031 g of palladium acetate, 4.7 g of bis(N, N-4-methylphenyl)-3,5-dichlorophenylamine (6), 11.9 g of bis(4'-methylbiphenylyl)amine (7), 11.9 g of sodium t-butoxide and 0.056 g of tri-t-butylphosphine in this order. The resulting mixture was heated to 105° C. while it was stirred, and was reacted at the temperature for 12 hours under stirring.

After the reaction was ceased by adding 400 mL of ethanol to the reaction mixture, the resulting solid was collected by filtration and purified by column chromatography. The obtained solid was recrystallized from 400 mL of toluene, thereby providing 7.5 g of white solid in a yield of 56%.

Elemental analysis (% by weight as $C_{72}H_{61}N_3$):

|  | C | H | N |
|---|---|---|---|
| Calculated: | 89.31 | 6.35 | 4.34 |
| Measured: | 89.14 | 6.70 | 4.16 |

Figure 2:
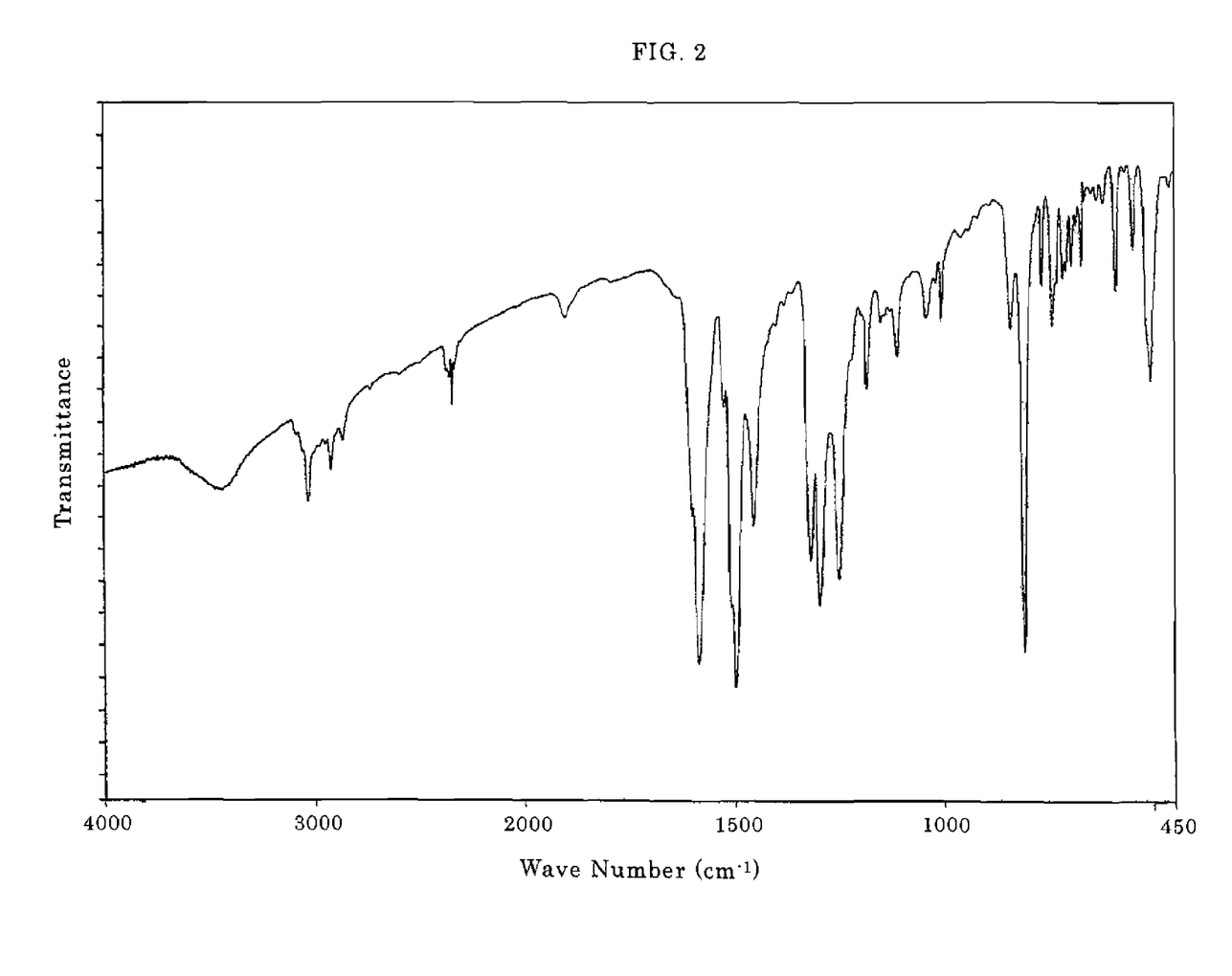
FIG. 2 is an infrared absorption spectrum of N,N,N',N'-tetrakis(4'-methyl-4-biphenylyl)-N'',N''-bis(4-methylphenyl)benzene-1,3,5-triamine (compound (3)), one of preferred 1,3,5-tris(diarylamino)-benzenes of the invention.
Figure 3:
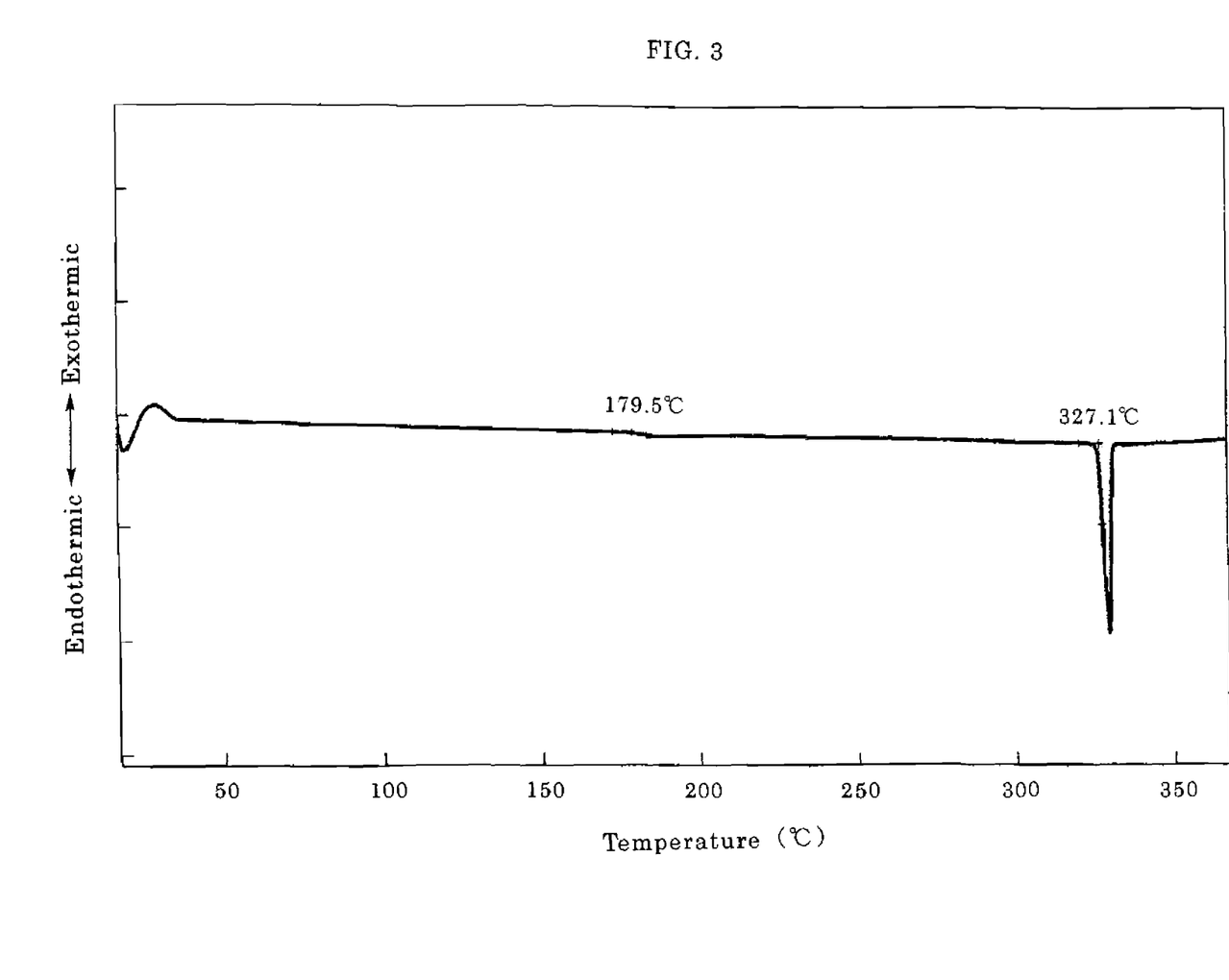
FIG. 3 is a DSC chart of the compound (3)

Mass analysis: (M+(m/e)): 967
Infrared Absorption Spectrum:
Measured by a KBr tablet method, and shown in FIG. 2.
Differential Scanning Calorimetry (DSC):
As the DSC chart is shown in FIG. 3, the compound (3) was found to have a glass transition temperature (Tg) of 179° C. and a melting point (Tm) of 327° C. The compound (3) is excellent in heat resistance. In contrast, the compound (1) has a glass transition temperature of 103° C. and a melting point of 278° C. whereas the compound (2) has a melting point of 408° C., but has no glass transition temperature as it is not observed.

Figure 4:
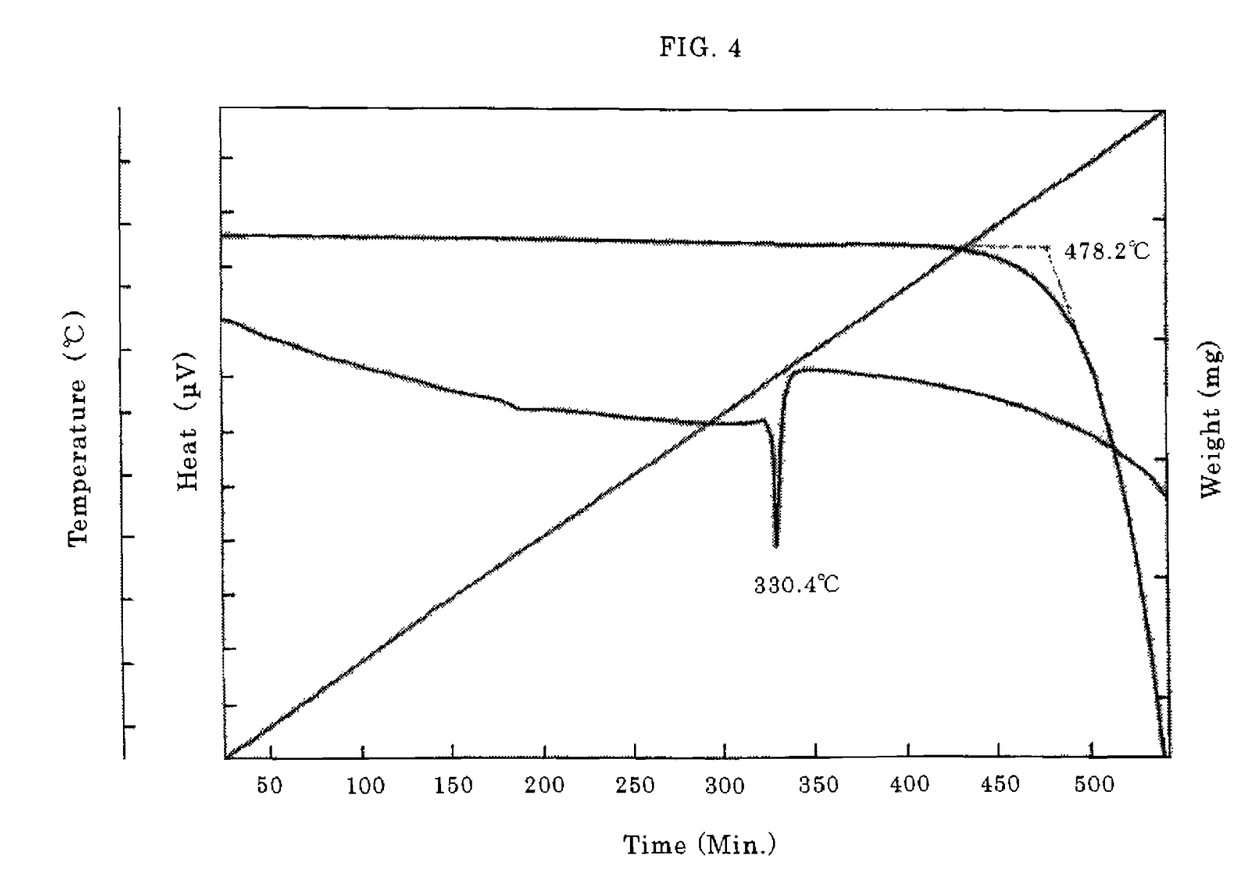
FIG. 4 is a TG/DTA chart of the compound (3)

Thermogravimetric Measurement/Differential Thermal Analysis (TG/DTA):
As the result is shown in FIG. 4, the compound (3) was found to have a decomposition temperature of 478° C. The compound (3) is excellent in heat resistance.

Figure 5:
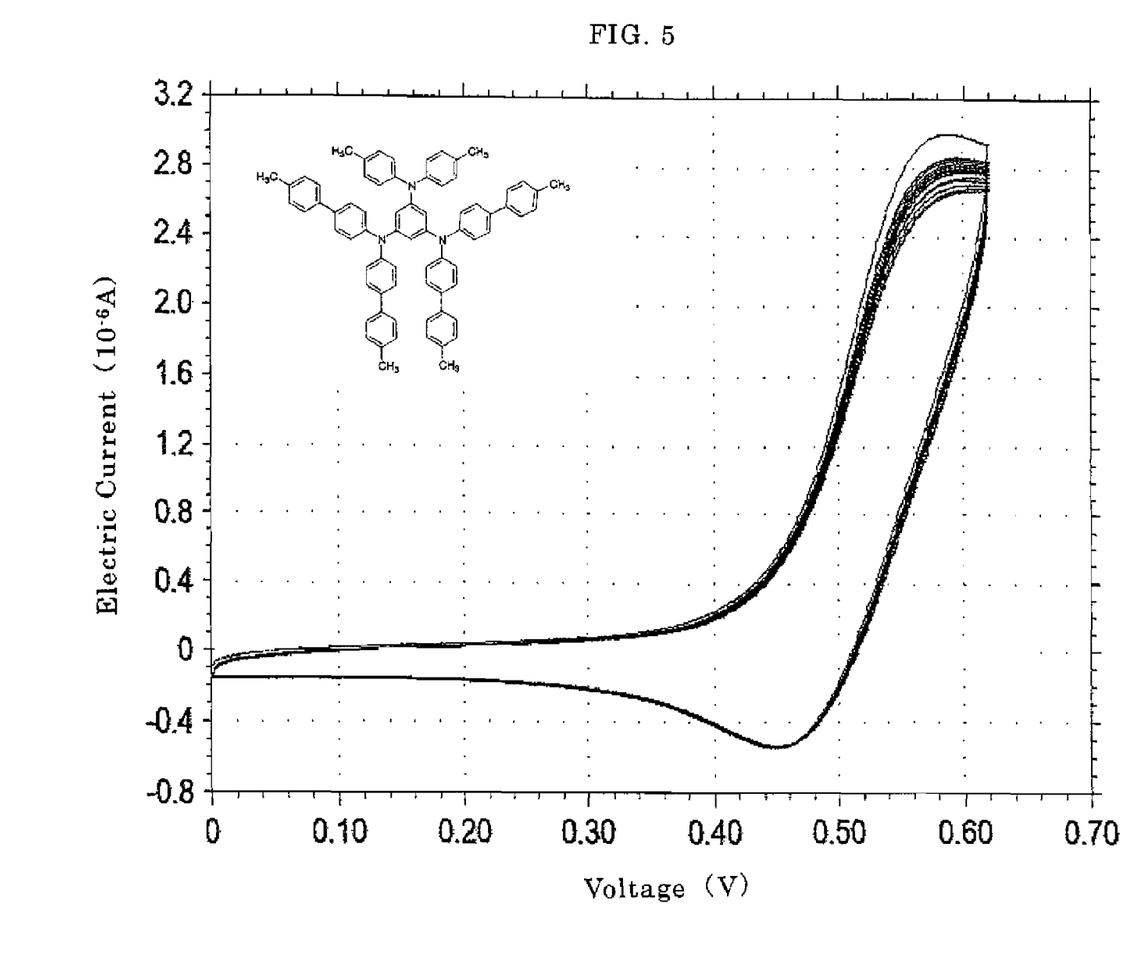
FIG. 5 is a CV chart of the compound (3)

Cyclic Voltammetry (CV):
As the CV chart is shown in FIG. 5, the oxidation potential was found to be 0.52 V (vs. Ag/Ag$^+$). Stability in repetition was found to be good, and the oxidation-reduction process was also found to be excellent in reversibility.

(Solubility Test):
500 mL of heated toluene was needed to dissolve 1 g of the compound (2), but 50 mL of heated toluene was needed to dissolve 1 g of the compound (3).

(Vacuum Evaporation Temperature Test)
The compound (3) was found to need a temperature of 350° C. to obtain an evaporation rate of 5 Å/second whereas the compound (2) a temperature of 415° C. As seen in the TG/DTA chart of the compound (3), the temperature at which decomposition of the compound (3) starts (430° C.) is higher than the above-mentioned vacuum evaporation temperature (350° C.), so that it is expected that substantial decomposition of the compound (3) does not occur at the vacuum evaporation temperature. The residual on the vacuum evaporation boat before and after vacuum evaporation of the compound (3) was analyzed by high performance liquid chromatography, showing that the residual on the vacuum evaporation boat before and after vacuum evaporation was in fact found to have a purity of 100.00%.

In contrast, the compound (2) starts decomposition at a temperature of 412° C. as shown by the TG/DTA measurement. Since the temperature is close to the above-mentioned vacuum evaporation temperature (415° C.), it is expected that the compound (2) is accompanied by thermal decomposition at the vacuum evaporation temperature. The residual on the vacuum evaporation boat before and after vacuum evaporation of the compound (2) was analyzed by high performance liquid chromatography, showing that the residual on the vacuum evaporation boat before vacuum evaporation was found to have a purity of 99.03% whereas the residual after vacuum evaporation a purity of 95.87.

Example 2

(Synthesis of N,N,N',N'-tetrakis(4-biphenylyl)-N'', N''-bis(4-methyl-phenyl)benzene-1,3,5-triamine(4))

850 mL of xylene was placed in a 1 L-capacity separable flask, and then 0.045 g of palladium acetate, 6.9 g of bis(N, N-4-methylphenyl)-3,5-dichlorophenylamine (6), 16.0 g of bis(biphenylyl)amine, 17.3 g of sodium t-butoxide and 0.081 g of tri-t-butylphosphine in this order. The resulting mixture was heated to 105° C. while it was stirred, and was reacted at the temperature for 14 hours under stirring.

After the reaction was ceased by adding 800 mL of ethanol to the reaction mixture, the resulting solid was collected by filtration and purified by column chromatography. The obtained solid was recrystallized from 300 mL of toluene, thereby providing 6.4 g of white solid in a yield of 35%.

Elemental analysis (% by weight as $C_{68}H_{53}N_3$):

|  | C | H | N |
|---|---|---|---|
| Calculated: | 89.54 | 5.86 | 4.61 |
| Measured: | 89.33 | 5.91 | 4.76 |

Figure 6:
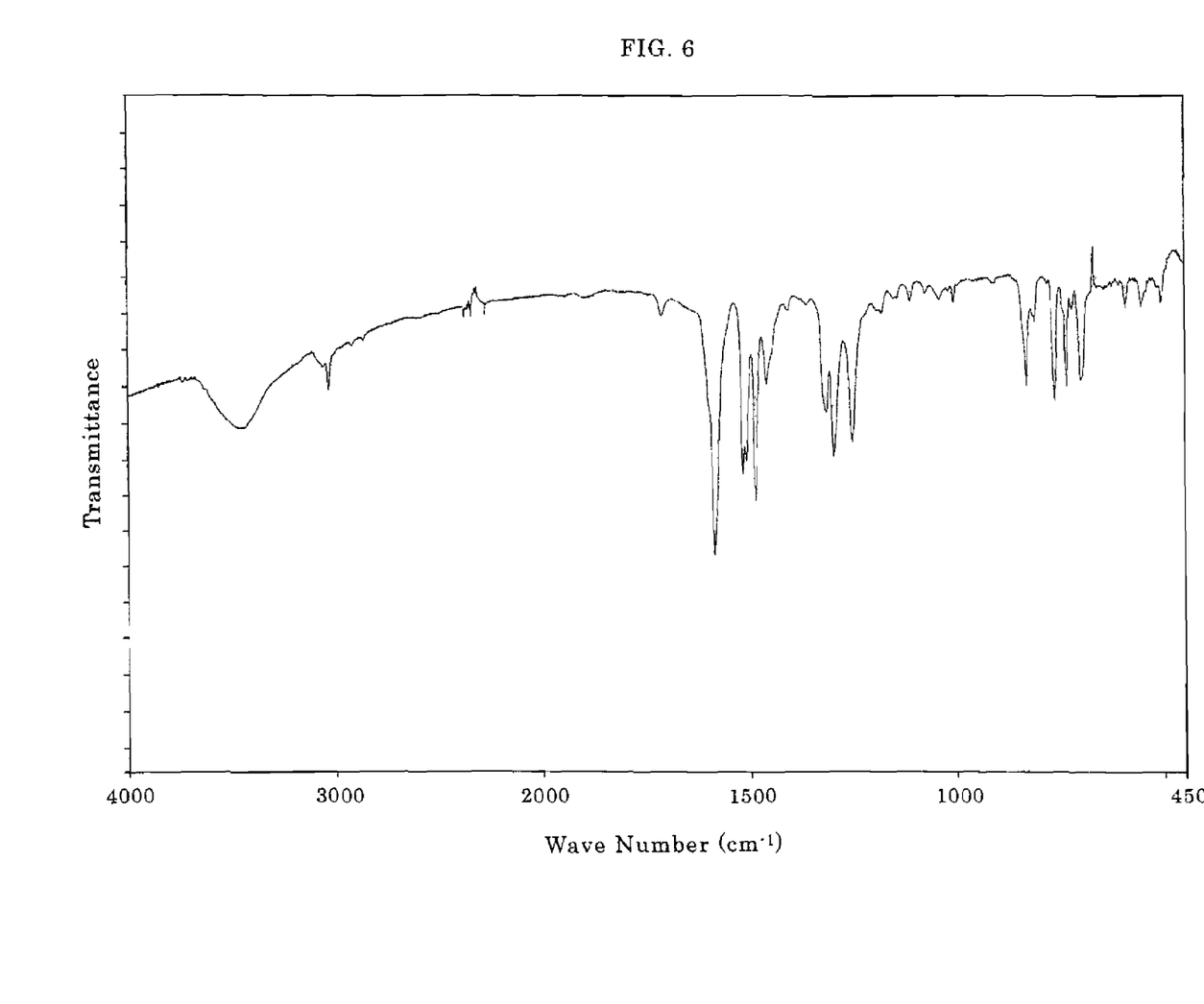
FIG. 6 is an infrared absorption spectrum of N,N,N',N'-tetrakis(4-biphenylyl)-N'',N''-bis(4-methylphenyl)benzene-1,3,5-triamine (compound (4)), one of preferred 1,3,5-tris(diarylamino)benzenes of the invention.
Figure 7:
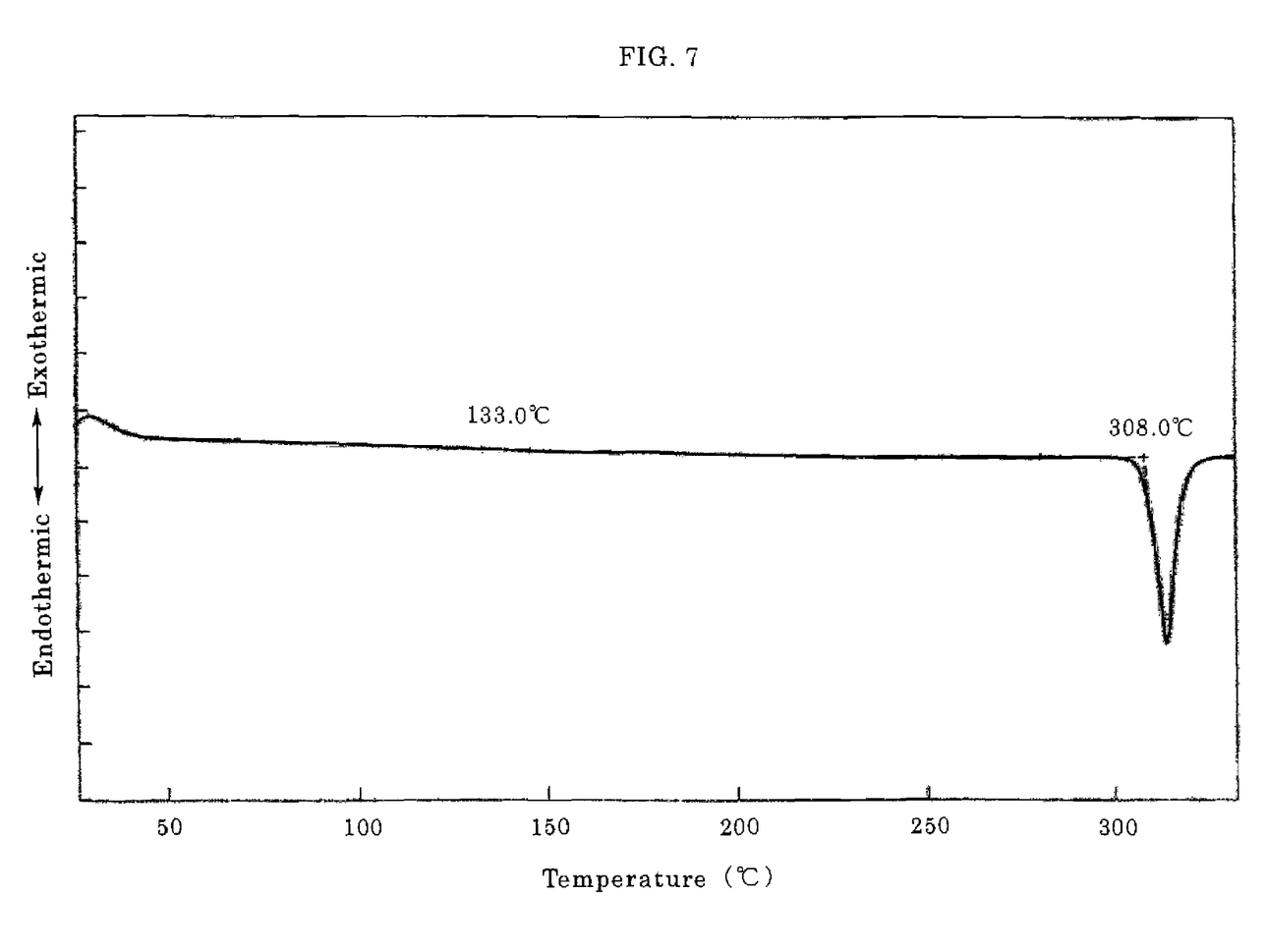
FIG. 7 is a DSC chart of the compound (4)

Mass analysis: (M+(m/e)): 912
Infrared Absorption Spectrum:
Measured by a KBr tablet method, and shown in FIG. 6.
Differential Scanning Calorimetry (DSC):
As the DSC chart is shown in FIG. 7, the compound (4) was found to have a glass transition temperature (Tg) of 133° C. and a melting point (Tm) of 308° C. The compound is excellent in heat resistance. In contrast, as mentioned hereinbefore, the compound (1) has a glass transition temperature of 103° C. and a melting point of 278° C. whereas the compound (2) has a melting point of 408° C., but no glass transition temperature as it is not observed.

Figure 8:
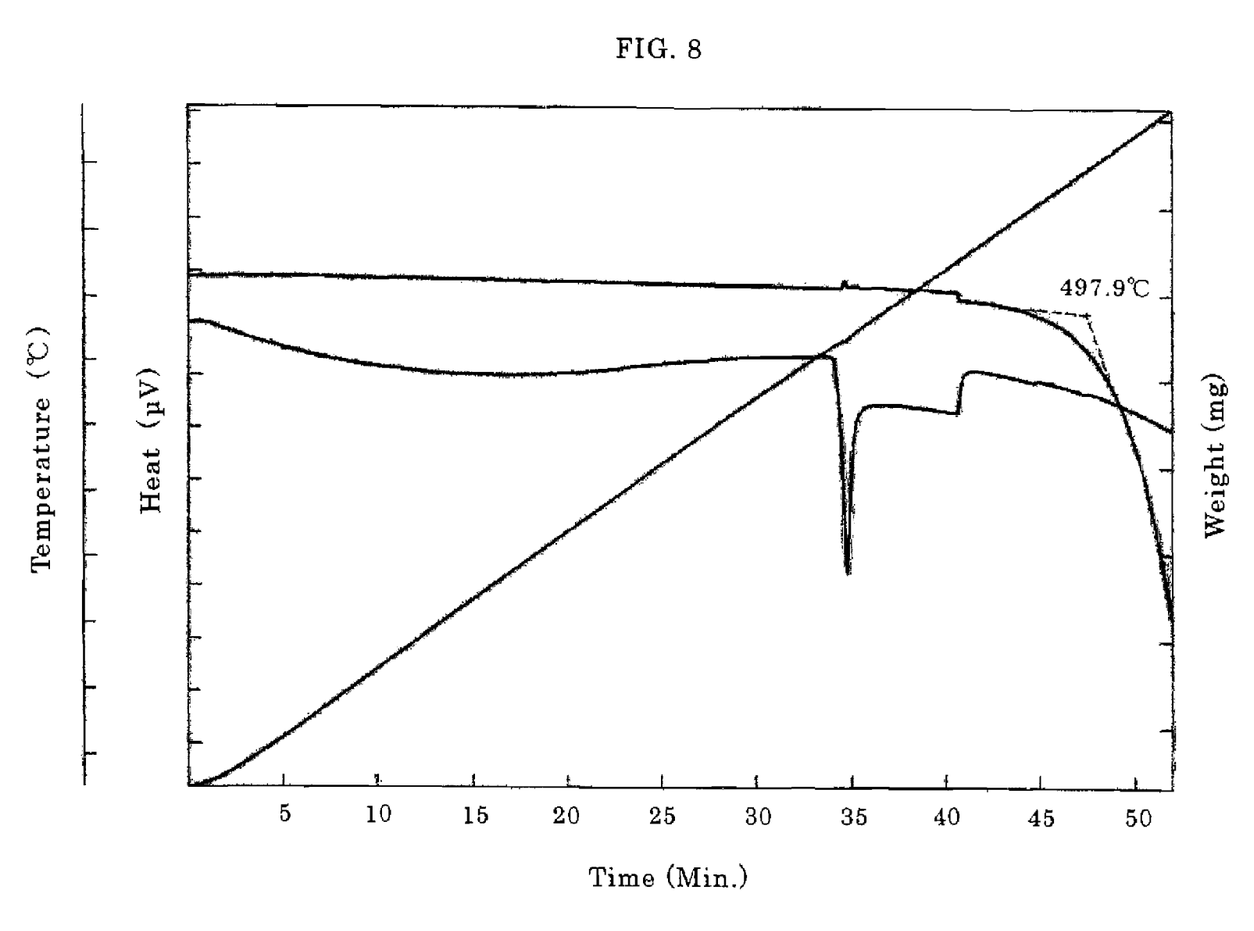
FIG. 8 is a TG/DTA chart of the compound (4)

Thermogravimetric Measurement/Differential Thermal Analysis (TG/DTA):

As the result is shown in FIG. 8, the compound (4) was found to have a decomposition temperature of 498° C. The compound (4) is excellent in heat resistance.

Figure 9:
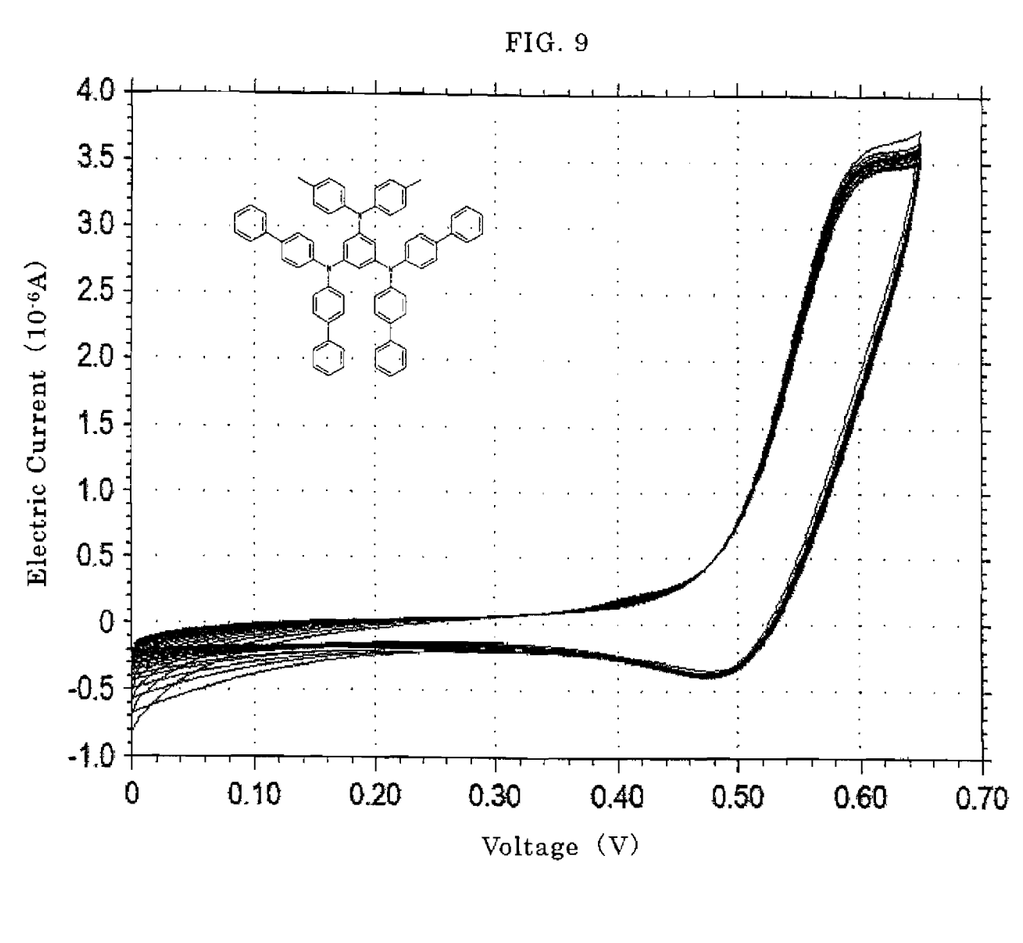
FIG. 9 is a CV chart of the compound (4).

Cyclic Voltammetry (CV):

As the CV chart is shown in FIG. 9, the oxidation potential was found to be 0.54 V (vs. Ag/Ag$^+$). Stability in repetition was found to be good, and the oxidation-reduction process was also found to be excellent in reversibility.

(Solubility Test):

500 mL of heated toluene was needed to dissolve 1 g of the compound (2), but 50 mL of heated toluene was needed to dissolve 1 g of the compound (4).

(Vacuum Evaporation Temperature Test)

The compound (4) was found to need a temperature of 340° C. to obtain an evaporation rate of 5 Å/second whereas the compound (2) a temperature of 415° C. As seen in the TG/DTA chart of the compound (4), the temperature at which decomposition of the compound (4) starts (498° C.) is higher than the above-mentioned vacuum evaporation temperature (340° C.), so that it is expected that substantial decomposition of the compound (4) does not occur at the vacuum evaporation temperature. The residual on the vacuum evaporation boat before and after vacuum evaporation of the compound (4) was analyzed by high performance liquid chromatography, showing that the residual on the vacuum evaporation boat before vacuum evaporation was found to have a purity of 99.30% and the residual on the vacuum evaporation boat after vacuum evaporation a purity of 99.64%.

Example 3

A sheet of plate glass having an ITO coating on one face (available from Sanyo Vacuum K.K.) was subjected to ultrasonic cleaning using acetone and then steam cleaning using methanol, followed by irradiation with ultraviolet rays by using a low-pressure mercury lamp for 10 minutes. Immediately after the irradiation, copper phthalocyanine (CuPC) was vacuum evaporated to form a hole injecting layer 20 nm thick and then the compound (3) was vacuum evaporated to form a hole transporting layer 10 nm thick in this order on the ITO coating by using a vacuum evaporation apparatus. Subsequently, an emission layer 75 nm thick was formed of tris(8-quinolinol)aluminum (Alq$_3$) on the hole transporting layer, and then a lithium fluoride layer 0.5 nm thick and an aluminum layer 100 nm thick were layered in this order on the emission layer to form a cathode, thereby providing an organic electroluminescence element.

This organic electroluminescence element was found to have a current efficiency 5.4 cd/A and an energy efficiency of 3.4 lm/W at a current density of 25 mA/cm$^2$, and a luminance half-life period of 14256 hours as defined by driving time until the luminance came to half the initial luminance of 1000 cd/m$^2$ and a maximum luminance of 33239 cd/m$^2$.

Example 4

A hole transporting layer 10 nm thick was formed by vacuum evaporation of the compound (4), and otherwise in the same manner as Example 3, an organic electroluminescence element was prepared. This organic electroluminescence element was found to have a current efficiency 5.2 cd/A and an energy efficiency of 3.3 lm/W at a current density of 25 mA/cm$^2$, and a luminance half-life period of 15862 hours as defined by driving time until the luminance came to half the initial luminance of 1000 cd/m$^2$ and a maximum luminance of 32910 cd/m$^2$.

Comparative Example 1

α-NPD was used as a hole transporting agent, and otherwise in the same manner as Example 2, an organic electroluminescence element was prepared. This organic electroluminescence element was found to have a current efficiency 4.0 cd/A and an energy efficiency of 2.2 lm/W at a current density of 25 mA/cm$^2$, and a luminance half-life period of 8019 hours as defined by driving time until the luminance came to half the initial luminance of 1000 cd/m$^2$ and a maximum luminance of 28710 cd/m$^2$.

The invention claimed is:

1. A 1,3,5-tris(diarylamino)benzene represented by the general formula (I)

(I)

wherein A and B are each independently a group represented by the general formula (II)

(II)

in which R is a hydrogen atom, an alkyl group of 1-6 carbons or a cycloalkyl group of 5 or 6 carbons and n is 0, 1, 2 or 3, provided that the values of n of A and B are not the same to each other.

2. A 1,3,5-tris(diarylamino)benzene according to claim 1 which is represented by the general formula (III)

(III)

wherein $R_1$ and $R_2$ are each independently a hydrogen atom, an alkyl group of 1-6 carbons or a cycloalkyl group of 5 or 6 carbons.

3. A 1,3,5-tris(diarylamino)benzene according to claim 1 which is represented by the general formula (IV)

(IV)

wherein $R_1$ and $R_2$ are each independently a hydrogen atom, an alkyl group of 1-6 carbons or a cycloalkyl group of 5 or 6 carbons.

4. A 1,3,5-tris(diarylamino)benzene according to claim 1 which is N,N,N',N'-tetrakis(4'-methyl-4-biphenylyl)-N",N"-bis(4-methylphenyl)- benzene-1,3,5-triamine.

5. A 1,3,5-tris(diarylamino)benzene according to claim 1 which is N,N,N',N'-tetrakis(4-biphenylyl)-N",N"-bis(4-methylphenyl)benzene- 1,3,5-triamine.

6. An organo-electronic functional material which comprises a 1,3,5-tris(diarylamino)benzene according to claim 1.

7. A hole injecting and/or transporting agent which comprises a 1,3,5-tris(diarylamino)benzene according to claim 1.

8. An organic electroluminescence element which comprises a hole injecting and/or transporting agent according to claim 7.

* * * * *